United States Patent [19]
Abnett

[11] Patent Number: 6,035,703
[45] Date of Patent: Mar. 14, 2000

[54] LOW VISCOSITY MEASUREMENT ADAPTER FOR AN ORBITING OBJECT VISCOMETER

[76] Inventor: Albert C. Abnett, 14250 T.H. 135, Nevada, Ohio 44849

[21] Appl. No.: 09/159,619

[22] Filed: Sep. 23, 1998

[51] Int. Cl.[7] .............................. G01N 11/12; G01N 11/14
[52] U.S. Cl. .......................................... 73/54.01; 73/54.28
[58] Field of Search .................................. 73/54.01, 54.23, 73/54.28, 54.31, 54.32

[56] References Cited

U.S. PATENT DOCUMENTS

| | | | |
|---|---|---|---|
| 1,334,856 | 3/1920 | Hayes et al. | 73/54.23 |
| 2,237,743 | 4/1941 | McIntyre | 265/11 |
| 2,491,639 | 12/1949 | Bechtel et al. | 73/59 |
| 3,107,520 | 10/1963 | Mouly et al. | 73/60 |
| 3,408,859 | 11/1968 | Konen | 73/54 |
| 3,496,762 | 2/1970 | Gaeta | 73/54 |
| 4,332,158 | 6/1982 | Osborne | 73/59 |
| 4,483,454 | 11/1984 | Rogers et al. | 220/5 A |
| 4,823,594 | 4/1989 | Gray | 73/54 |
| 4,863,055 | 9/1989 | Bietz | 220/5 A |
| 5,031,795 | 7/1991 | Kotera et al. | 220/563 |
| 5,212,981 | 5/1993 | Laun et al. | 73/54.01 |
| 5,232,246 | 8/1993 | Page | 280/837 |
| 5,292,193 | 3/1994 | Funk | 366/307 |
| 5,365,777 | 11/1994 | Layton | 73/54.28 |
| 5,394,739 | 3/1995 | Garvey, III et al. | 73/54.23 |
| 5,520,270 | 5/1996 | Hornung et al. | 188/266 |
| 5,546,791 | 8/1996 | Meeten | 73/54.28 |
| 5,798,454 | 8/1998 | Nakazeki et al. | 73/54.28 |

*Primary Examiner*—Hezron Williams
*Assistant Examiner*—J. David Wiggins
*Attorney, Agent, or Firm*—David G. Herold

[57] ABSTRACT

An adapter for an orbiting object viscometer that extends the practical measurement range of such viscometer type to lower viscosity fluids and improves the measurement accuracy. A baffle means disposed in the test fluid reduces whirlpooling, which occurs in low useful viscosity fluids, to extend the viscosity measurement range to lower viscosity fluids. A temperature sensor disposed in the test fluid increases the accuracy of the viscosity measurements by providing more accurate fluid temperature to the processor calculating the viscosity. The advantages of the orbiting object viscometer such as rapid viscosity measurements and the ability to measure the viscosity of hazardous or corrosive fluids are maintained through the design of the adapter providing support for a single vane baffle or compound vane baffle immersed into the fluid, which adaptor is designed and mounted to ensure that the baffle carefully avoids the path of the orbiting object within same fluid.

8 Claims, 4 Drawing Sheets

LOW VISCOSITY MEASUREMENT ADAPTER FOR AN ORBITING OBJECT VISCOMETER

BACKGROUND

1. Field of Invention

The present invention relates generally to viscosity measurements and specifically to improvements to an orbiting object viscometer in the areas of extending the range of such a device to lower viscosity fluids and improving the accuracy of the measurements.

2. Description of Prior Art

The accurate measurement of the viscosity of a fluid is important in a variety of commercial and scientific endeavors. Accordingly, the orbiting object viscometer was developed with the goal of making a viscosity measurement that can be done quickly and which produces accurate and repeatable results for fluids having a wide range of viscosities.

The orbiting object viscometer disclosed in U.S. Pat. No. 5,394,739 measures viscosity by magnetically propelling a magnetic object through a fluid in an orbital pattern. By controlling the magnetic drive parameters and by measuring the resulting behavior of the magnetic object in the fluid and the fluid temperature, accurate and repeatable viscosity values may be calculated. However, when measuring low viscosity fluids, whirlpooling in the fluid causes gross inaccuracies in the calculated results. In addition, measuring fluid temperature through the wall of the receptacle containing the fluid adds variance to the results due to self-heating of the temperature sensor by the measurement apparatus.

A whirlpool reduction device is disclosed in U.S. Pat. No. 5,232,246. This device reduces whirlpooling in fluid entering a drain pipe for the purpose of increasing fluid flow through the drain pipe. The baffles described in patent '246 are not adaptable to the viscosity measurement application for several reasons. The forces causing whirlpools in the two applications are different so the design of the baffles must be different due to differing requirements. The viscosity measurement application has no fluid outflow so that the design and positioning of baffles in the two applications are completely different. In addition, the baffles disclosed in patent '246 are not readily removeable.

What is needed then, is a device that may be used with an orbiting object viscometer, that reduces whirlpooling in low viscosity fluids and provides accurate fluid temperature measurements for use in the viscosity calculations and which is easily removable so that the inherent qualities of the orbiting object viscometer, such as rapid viscosity testing, are maintained.

OBJECTS AND ADVANTAGES

An object of the low viscosity measurement adapter of the present invention is to extend the useful measurement range of an orbiting object viscometer to lower viscosity fluid.

A further object of the low viscosity adapter is to improve the accuracy of the viscosity measurements produced by an orbiting object viscometer.

Another object of the present invention is to maintain the ability of the orbiting object viscometer to make rapid viscosity practical measurements while extending the measurement range to lower viscosities and improving the accuracy of the measurements.

Another object of the present invention is to maintain the ability of the orbiting object viscometer to measure the viscosity of hazardous or corrosive fluids while extending the measurement range to lower viscosities and improving the accuracy of the measurements.

SUMMARY

These and related objects of the invention are achieved in a low viscosity adapter used in conjunction with an orbiting object viscometer. An orbiting object viscometer includes a receptacle that holds a fluid sample to be tested and a magnetic object. The receptacle is surrounded by a magnetic drive mechanism that propels the magnetic object through the test fluid in a generally orbital pattern. Sensors under the receptacle detect the movement and position of the orbiting object and produce signals corresponding to fluid viscosity. An associated processor accepts data from the sensors and combines that with magnetic drive parameters and fluid temperature and calculates the viscosity of the fluid.

The low viscosity adapter includes a baffle extending into the test fluid that resists the tendency of low viscosity fluids to follow the path of the orbiting object, creating a whirlpool. Reduction of whirlpooling allows the orbiting object viscometer to accurately measure lower viscosity fluids.

The low viscosity adapter also includes a temperature sensor that directly measures the temperature of the test fluid in the vicinity of the orbiting object. Accurate fluid temperature is a critical parameter in the viscosity calculation. This invention greatly improves the accuracy of the viscosity measurement by providing accurate fluid temperature to the processor calculating fluid viscosity.

The low viscosity adapter is easily removable for cleaning or disposal of replaceable parts. When used with an orbiting object viscometer that accepts a disposable test cup, placed in the receptacle, the test fluid and everything it has touched may be disposed of and the apparatus is ready to test another fluid sample. This feature maintains the advantages of the orbiting object viscometer of rapid viscosity measurements and the ability to make viscosity measurements on hazardous or corrosive fluids.

REFERENCE NUMERALS

Figure 1:
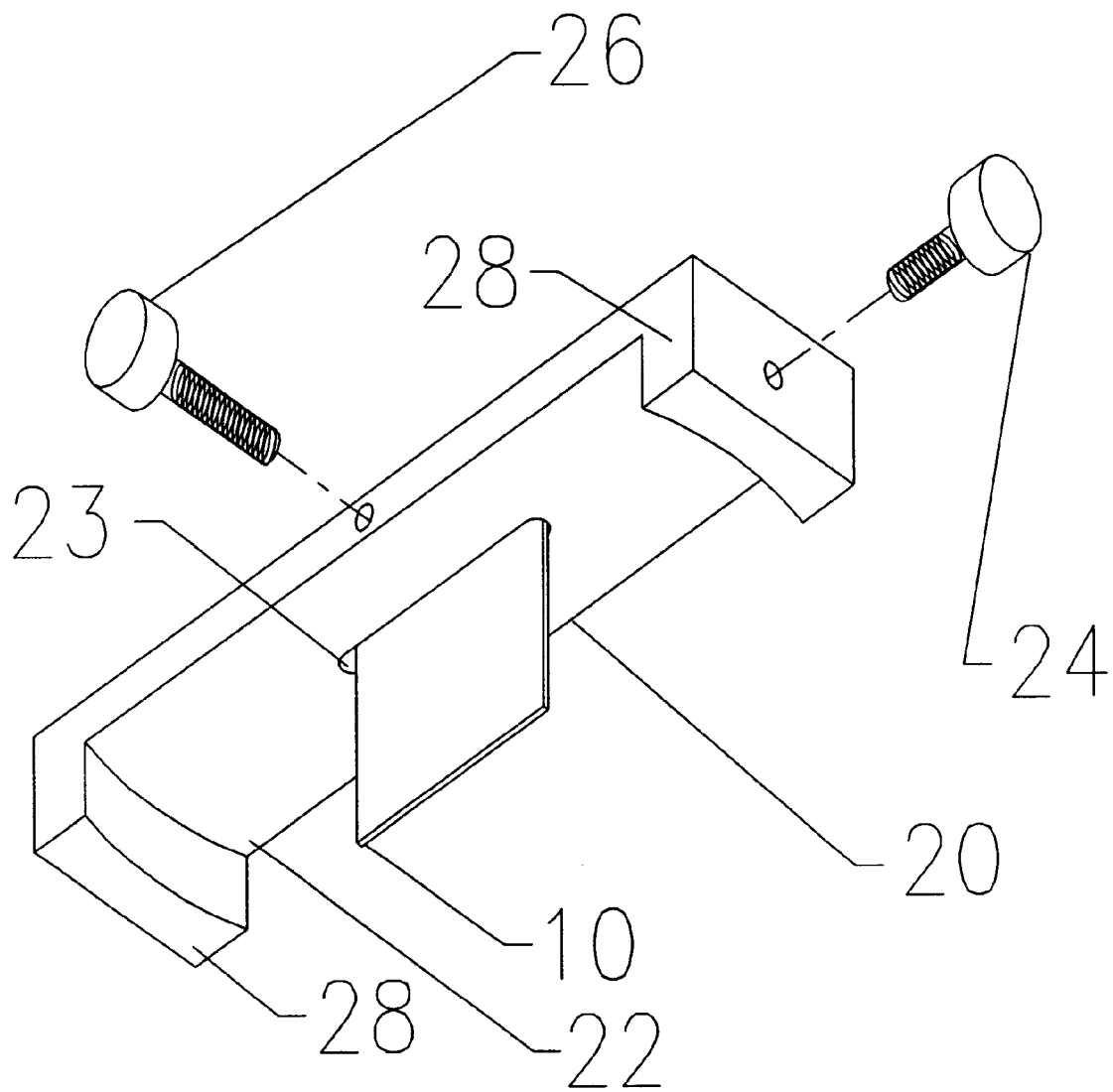
FIG. 1 is a perspective view of the underside of the low viscosity adapter showing the single vane baffle and the bridge.
Figure 2:
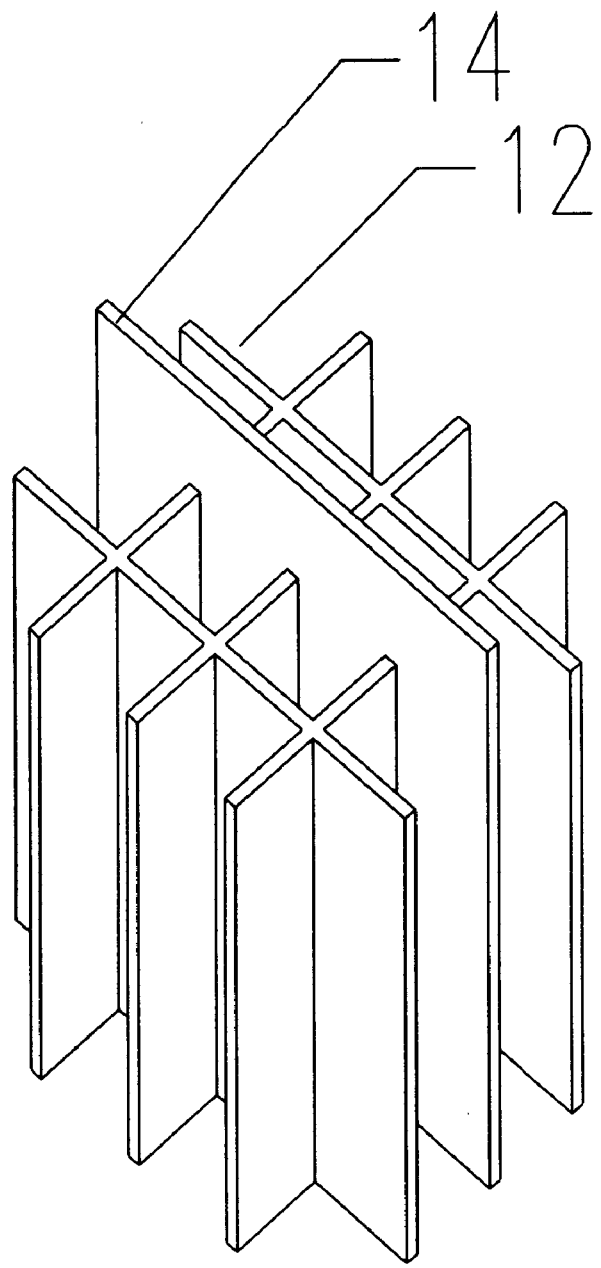
FIG. 2 shows a compound baffle.
Figure 3:
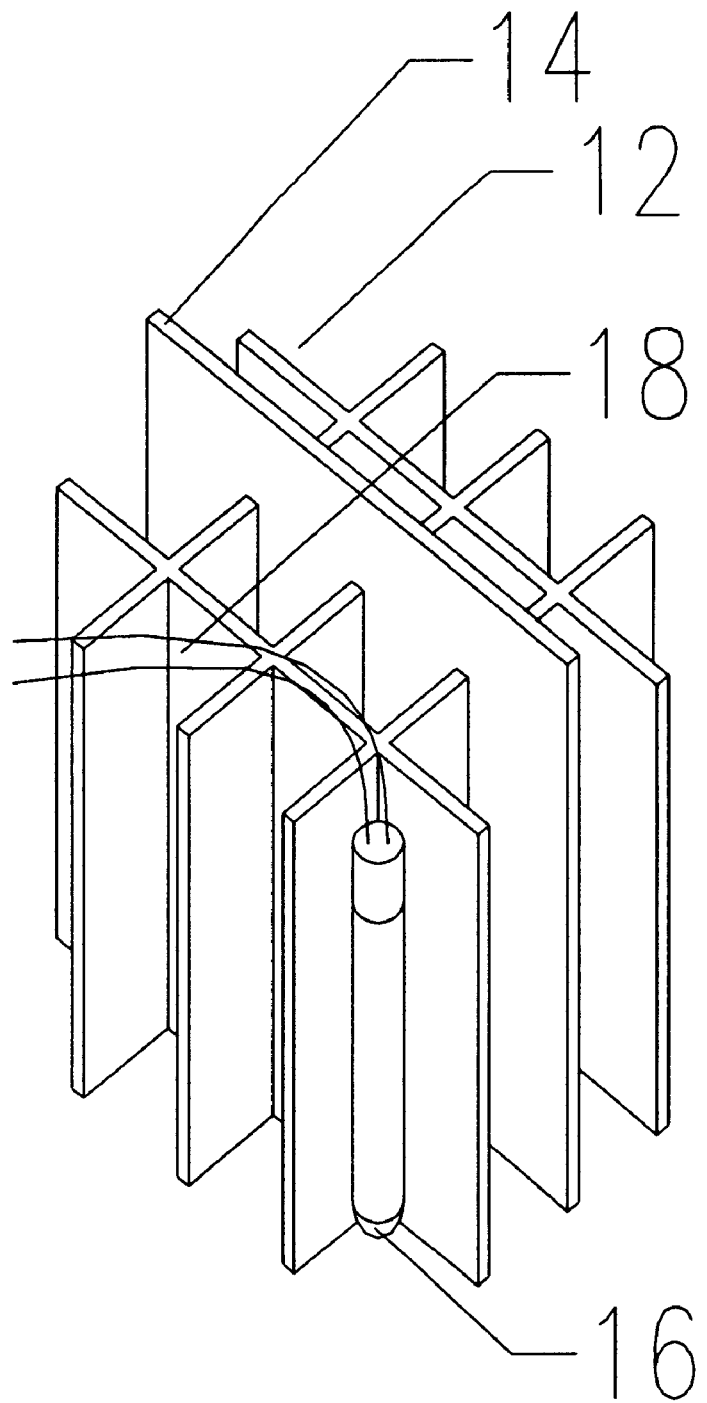
FIG. 3 shows a compound baffle with attached temperature probe.

10 Single vane baffle
12 Compound baffle
14 Baffle attachment tab
16 Temperature sensor
18 Temperature sensor wires
20 Bridge
22 Span
23 Notch
24 Bridge retention fastener
26 Baffle retention fastener
28 Fingers
30 Receptacle 32 Test fluid 34 Orbiting object when in motion; magnetic object when at rest

DESCRIPTION—FIGS. 1 THROUGH 4

An orbiting object viscometer includes an open receptacle 30 that holds a fluid sample 32 to be tested and a magnetic object 34.

The low viscosity measurement adapter consists of a bridge 20 spanning the opening of receptacle 30. Bridge 20 consists of a span 22 with fingers 28 descending from each end that engage the outer lip of receptacle 30. A set screw 24 extends through one of the fingers 28 to provide a removable connection to receptacle 30 at its outer lip. Span 22 also includes a notch 23 on the under side for the purpose of retaining baffle 10. A set screw 26 extends through span 22 into notch 23 to provide a removable connection to the bridge 20 for the single baffle 10.

Baffle 10 extends through the opening in receptacle 30 into test fluid 32 above orbiting object 34. Temperature sensor 16 is attached to baffle 10 (not shown) and is disposed into test fluid 32 proximal to orbiting object 34.

A compound baffle 12 is also shown in the figures and represents a second preferred embodiment. Compound baffle 12, formed from multiple vanes, connects to bridge 20 via baffle attachment tab 14, in much the same way as baffle 10, and extends through the opening in receptacle 30 into test fluid 32 above orbiting object 34. Temperature sensor 16 is attached to baffle 12 and is disposed into test fluid 32 proximal to orbiting object 34.

OPERATION—FIGS. 1 THROUGH 4

An orbiting object viscometer includes an open receptacle 30 that holds a fluid sample 32 to be tested and a magnetic object 34. Receptacle 30 is surrounded by a magnetic drive mechanism (not shown) that propels the magnetic object 34 through test fluid 32 in a generally orbital pattern. Sensors (not shown) under receptacle 30 detect the movement and position of orbiting object 34 and produce signals corresponding to fluid viscosity. An associated processor (not shown) accepts data from the sensors and combines that with magnetic drive parameters and fluid temperature to calculate the viscosity of the fluid.

At low viscosity, test fluid 32 tends to follow the path of orbiting object 34, creating a whirlpool. As the viscosity of the test fluid gets lower, orbiting object 34 eventually breaks out of the test fluid into the resulting whirlpool and the accuracy of the viscosity calculations are reduced. Calculation accuracy is reduced because the viscosity calculation is based on the movement of the orbiting object through the test fluid. The movement of the orbiting object changes based on the opposing force encountered in propelling the object through the test fluid. Those forces change dramatically if the object breaks out of the test fluid.

The present invention extends the range of accurate viscosity measurements to lower viscosity fluids by introducing a baffle into test fluid 32 above orbiting object 34 such that whirlpooling in test fluid 32 is reduced. Accurate viscosity measurements can be made as long as the orbiting object remains completely immersed in the test fluid throughout its orbital path.

Figure 4:
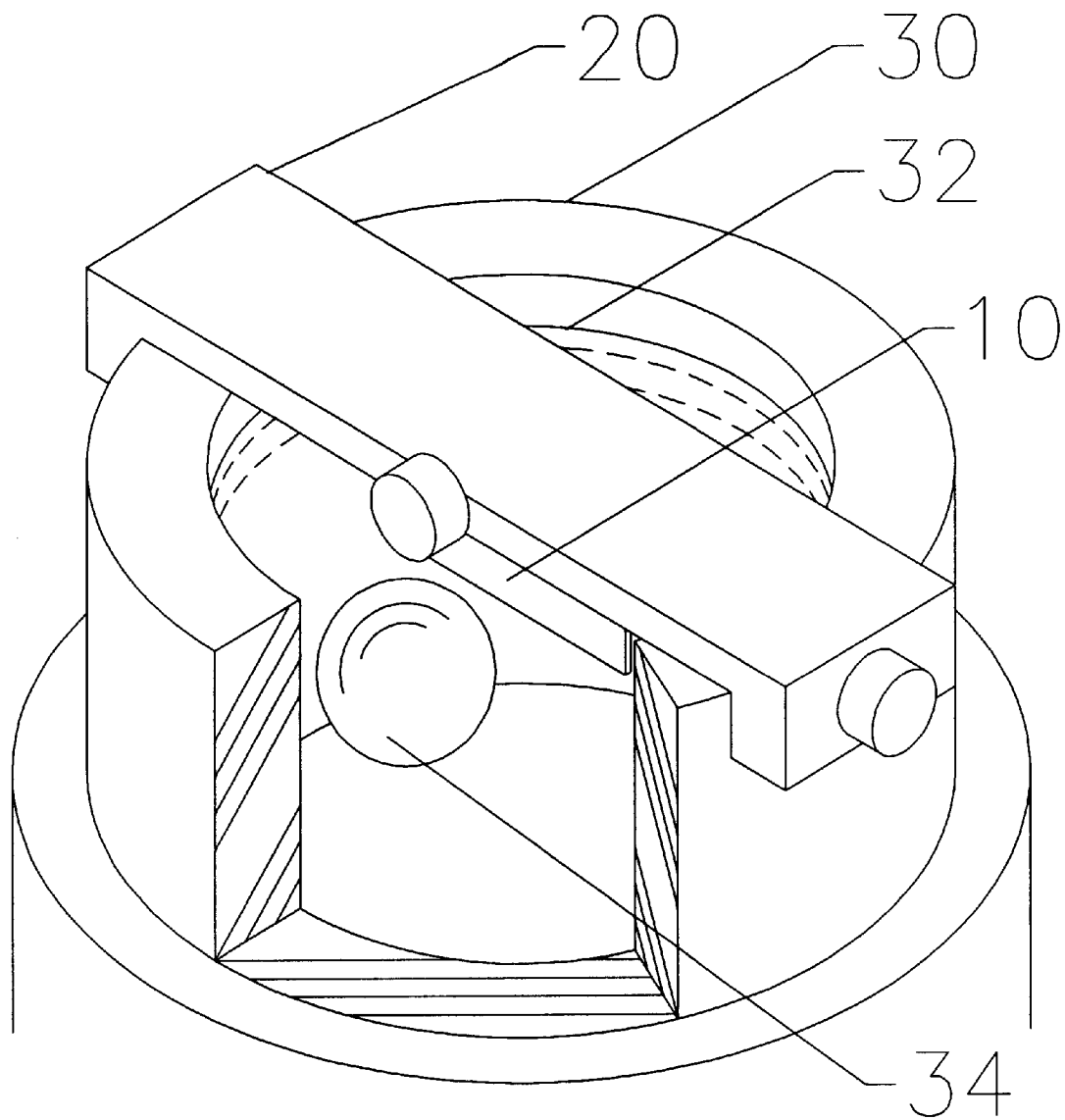
FIG. 4 shows a cut away view of an orbiting object viscometer with the low viscosity measurement adapter installed.

In one embodiment, the low viscosity adapter of the present invention consists of a single baffle 10 removably connected to bridge 20 that spans the opening at the top of the receptacle 30 of the orbiting object viscometer. In a second preferred embodiment the present invention consists of a compound baffle 12, formed from multiple vanes, removably connected to bridge 20. In either of the preferred embodiments, a temperature sensor may be included with, and attached to, the baffle. In both of the preferred embodiments, the baffle is positioned in the test fluid 32 above the orbiting object 34 within the receptacle 30 of the orbiting object viscometer. FIG. 4 shows the low viscosity adapter mounted on the receptacle 30 of an orbiting object viscometer. Bridge retention fastener 24 is used to hold bridge 20 stationary with respect to receptacle 30. The single baffle 10 or compound baffle 12 assembly is connected to bridge 20 via baffle retention fastener 26. Baffle 10 or 12 is held stationary with respect to receptacle 30, and extends through the opening in the receptacle into test fluid 32 above the path of orbiting object 34.

The orbiting object viscometer described in U.S. Pat. No. 5,394,739 operates accurately down to a viscosity of approximately 20 centipoise. At viscosities below approximately 20 centipoise, the orbiting object begins to break out of the test fluid 32 because of whirlpooling in test fluid 32 and the accuracy of the measurement suffers. The single vane baffle 10 reduces the whirlpooling effect and allows accurate measurement of viscosity down to approximately 2 centipoise. At viscosities below 2 centipoise, the accuracy of viscosity measurements is again reduced by sloshing of the fluid parallel to the baffle. Compound baffle 12 further reduces fluid movement such that accurate measurements may be made down to approximately 0.3 centipoise.

Fluid temperature is critical to the accurate calculation of viscosity. The orbiting object viscometer may include an integral temperature sensor, but self-heating by the device reduces the accuracy of the temperature measurement. Further, if a test cup is used within the receptacle, the integral temperature sensor is in indirect contact with the test fluid and the temperature measurement is even less accurate. Including a temperature sensor with the low viscosity adapter greatly improves the accuracy of the test fluid temperature measurement and the accuracy of the viscosity measurement which is in part based on the measurement of test fluid temperature. Temperature sensor 16 is attached to the baffle in both preferred embodiments and directly measures test fluid temperature. Fluid temperature is communicated to the processor which calculates fluid viscosity via temperature sensor wires 18.

The materials of the preferred embodiments are anodized aluminum for the bridge and inert plastic for the baffles. Specific plastics applicable for the baffles are Teflon which is inert to most chemicals, but is soft and not moldable. Moldable plastics are polyphenylene sulfide or polypropylene. The attachment of the temperature sensor to the baffle includes being molded inside the baffle.

Although the description above contains many specificities, these should not be construed as limiting the scope of the invention but as merely providing illustrations of some of the presently preferred embodiments of this invention. For example the baffles could be formed from a different number or pattern of vanes and still remain within the scope of this patent.

Thus the scope of the invention should be determined by the appended claims and their legal equivalents, rather than by the examples given.

What is claimed is:

1. An apparatus for extending the measurement range for satisfactory accuracy of an orbiting object viscometer to lower viscosity fluid, said orbiting object viscometer including a receptacle for containing said fluid, an orbiting object disposed in said fluid in said receptacle that is driven to revolve in a path thru said fluid and a processor for calculating fluid viscosity, said apparatus comprising:

(a) an attachment means removably connected to said receptacle at a receptacle access opening and positioned over the opening in said receptacle;

(b) a whirlpool reduction means that prevent said orbiting object from breaking out of the fluid into a fluid formed whirlpool, with said whirlpool reduction means extending into said fluid in said receptacle by a supporting arrangement, with said whirlpool reduction means avoiding the path of said orbiting object; and (c) said whirlpool reduction means removably connected to said attachment means.

2. The apparatus of claim 1 wherein said whirlpool reduction means is a single vane baffle.

3. The apparatus of claim 2 further comprising a temperature sensor attached to said baffle disposed in said fluid proximal to said orbiting object, said temperature sensor providing fluid temperature to said processor.

4. The apparatus of claim 1 wherein said whirlpool reduction means is a compound baffle formed from multiple vanes.

5. The apparatus of claim 4 further comprising a temperature sensor attached to a vane among the multiple vanes on said baffle disposed in said fluid proximal to said orbiting object, said temperature sensor providing fluid temperature to said processor.

6. An apparatus for extending the measurement range for satisfactory accuracy of an orbiting object viscometer to lower viscosity fluid, said orbiting object viscometer including an open receptacle having a receptacle access opening and receptacle walls for containing said fluid, an orbiting object disposed in said fluid in said receptacle that is driven to revolve in a path thru said fluid and a processor for calculating fluid viscosity, said apparatus comprising:

a) a bridge spanning the opening of said receptacle above an outside lip on said receptacle, said bridge having two ends and a span, said span containing a notch oriented toward the receptacle;

b) fingers descending from each end of the bridge engage the outside lip of the receptacle, thereby supporting said bridge;

c) said bridge removably attached to said receptacle by a set screw threadedly engaged through one of said fingers and impinging on said receptacle;

d) a baffle means removably attached in said notch to said bridge by a second set screw, threadedly engaged in said span;

e) said baffle means extending through the opening in said receptacle into said fluid as supported by said bridge span to maintain a level of baffle immersion in the fluid, above the path of said orbiting object, thereby reducing whirlpooling and its associated whirlpool induced measurement inaccuracy by preventing said orbiting object from breaking out of the fluid into a fluid formed whirlpool; and f) a temperature sensor attached to said baffle disposed in said fluid proximal to said orbiting object, said temperature sensor providing fluid temperature to said processor.

7. The apparatus of claim 6 where the baffle means is a single vane baffle.

8. The apparatus of claim 6 where the baffle means is a compound baffle composed of multiple interconnecting vanes.

* * * * *